United States Patent [19]

Alley et al.

[11] 4,202,714

[45] May 13, 1980

[54] BALLISTIC MODIFIERS AND SYNTHESIS OF THE BALLISTIC MODIFIERS

[75] Inventors: Bernard J. Alley, Huntsville; James D. Dake, Redstone Arsenal; Hiram W. H. Dykes, Huntsville, all of Ala.

[73] Assignee: The United States of America as represented by the Secretary of the Army, Washington, D.C.

[21] Appl. No.: 316,600

[22] Filed: Dec. 20, 1972

Related U.S. Application Data

[62] Division of Ser. No. 58,133, Sep. 11, 1970.

[51] Int. Cl.$^2$ .......................................... C06B 23/00
[52] U.S. Cl. .............................. 149/109.4; 260/429.9; 260/430; 260/435 R; 260/438.1; 260/439 R; 260/447; 149/92; 149/98
[58] Field of Search ................ 260/435 R, 438.1, 430, 260/439, 429.9, 447; 149/98, 92, 109.4

[56] References Cited

U.S. PATENT DOCUMENTS

| 3,032,972 | 5/1962 | Preckel | 149/98 X |
|---|---|---|---|
| 3,088,858 | 5/1963 | Camp | 149/98 X |
| 3,103,458 | 9/1963 | Besser et al. | 149/98 |
| 3,138,499 | 6/1964 | Camp et al. | 149/98 X |
| 3,228,338 | 1/1966 | McEwan et al. | 149/98 |
| 3,228,815 | 1/1966 | Henry et al. | 149/98 |
| 3,379,010 | 4/1968 | Harvey | 149/98 |

*Primary Examiner*—Stephen J. Lechert, Jr.
*Attorney, Agent, or Firm*—Nathan Edelberg; Robert P. Gibson; James T. Deaton

[57] ABSTRACT

A new class of ballistic modifiers and the synthesis thereof is disclosed herein and are used in propellants either individually or as admixtures in percentages of approximately 0.5 to 6 weight percent to impart mesa or plateau burning rate characteristics over a wide pressure range and reduce the temperature sensitivity of the propellants in relation to burning rates. The modifiers are chelate type compounds comprised of lead and/or copper, and various predetermined molar ratios of compounds such as salicylic acid and beta-resorcylic acid.

18 Claims, 2 Drawing Figures

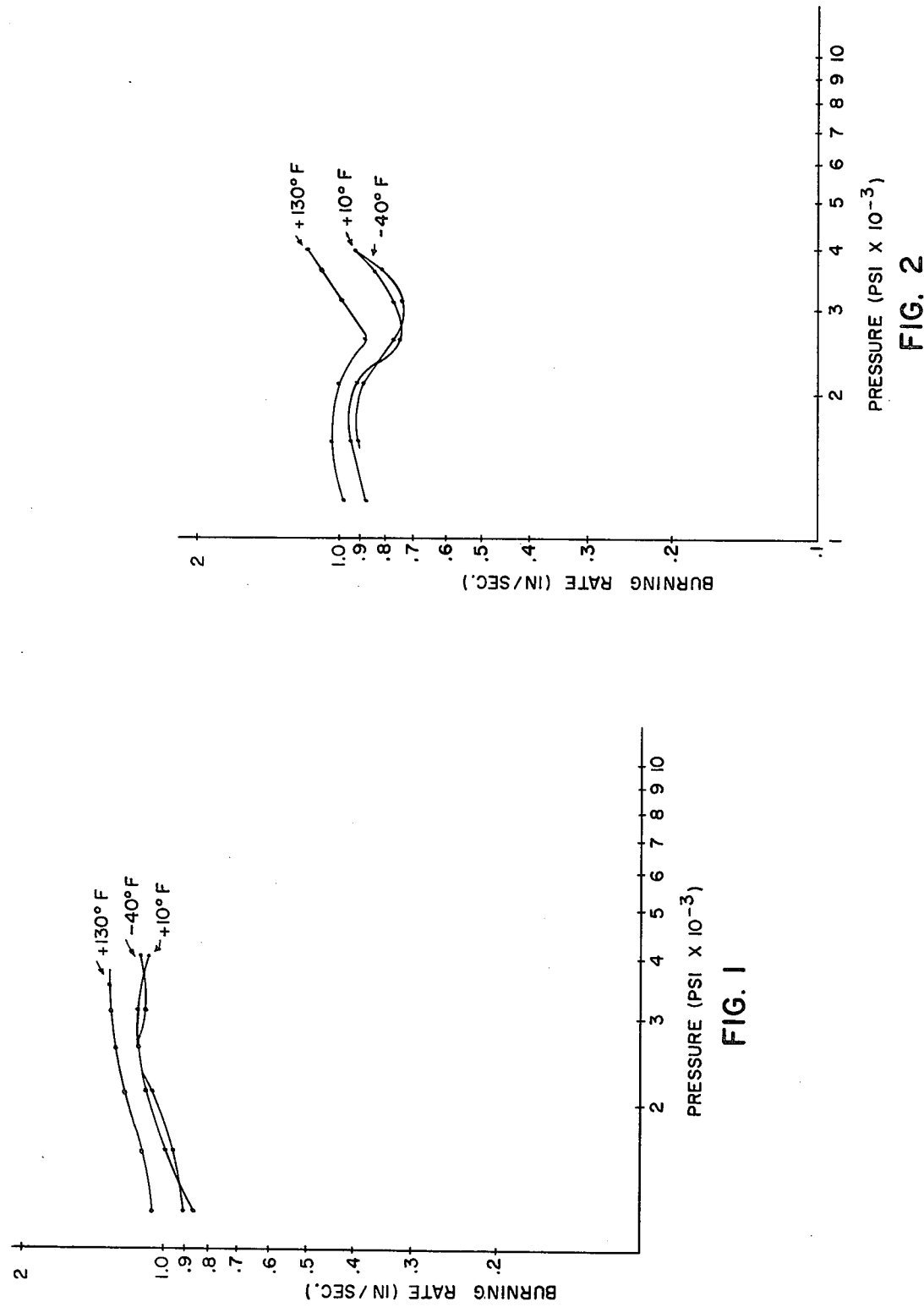

BALLISTIC MODIFIERS AND SYNTHESIS OF THE BALLISTIC MODIFIERS

CROSS REFERENCE TO RELATED APPLICATION

This application is a division of applicants' co-pending application Ser. No. 58,133, filed Sept. 11, 1970.

BACKGROUND OF THE INVENTION

Existing similar modifiers of the type disclosed herein give suitable propellant ballistic modification, but in general the existing modifiers are chemically unstable and hydrolyze during propellant processing and storage to create serious problems. The monobasic cupric salicylate and lead beta-resorcylate modifiers system currently used in the DRAGON side thruster and canister motors is an example of such an unstable system. The excess lead beta-resorcylate hydrolyzes to give beta-resorcylic acid as a product. The acid subsequently concentrates on the propellant surface and causes propellant ignition failures at low temperatures. As a result of this inadequate modifier, propellants with the inadequate modifier must be rejected. Therefore, it is an object of this invention to provide ballistic modifiers that are stable and do not cause adverse side effects when incorporated into propellant compositions.

Another object of this invention is to provide a novel process of synthesizing ballistic modifiers according to this invention.

A further object of this invention is to provide ballistic modifiers that can be used in solvent, solventless and casting powder type processes.

Still another object of this invention is to provide ballistic modifiers that are especially adapted for use with double base propellants.

A still further object of this invention is to provide ballistic modifiers in propellant compositions to produce mesa and/or plateau burning rate characteristics.

SUMMARY OF THE INVENTION

This invention relates to chelate type ballistic modifiers for double base propellants and the processes of synthesis of the ballistic modifiers. The ballistic modifiers are synthesized by either reacting metal ions with chelating agents in a reaction liquid or by reacting chelating agents that already contain metal with each other in the presence of a reacting liquid. The reaction is carried out from about room temperature up to about 100° C. The temperature at which the reaction takes place is chosen according to the speed of reaction desired. Reaction is faster at the higher temperature. The ballistic modifiers of this invention are utilized in double base propellants containing other ingredients such as nitrocellulose, nitroglycerine, Di-n-propyl adipate, 2-nitrodiphenylamine, candelilla wax and other desired ingredients as appropriate.

BRIEF DESCRIPTION OF THE DRAWING

FIG. 1 is a graph showing burning rate versus pressure of propellant Composition-E as illustrated in Table IV herein below; and FIG. 2 is a graph showing burning rate versus pressure of propellant Composition-F as illustrated in Table IV herein below.

DESCRIPTION OF THE PREFERRED EMBODIMENT

The new chelate type ballistic modifiers described in this invention are a significant advancement in ballistic modifier technology for double base propellants. When they are used in amounts of approximately 0.5 to 6-percent by weight in double base propellants, they impart mesa and/or plateau burning rate characteristics to the propellant over a wide pressure range, and reduce its temperature sensitivity ($\pi_K$). A significant property of these modifiers is that they are very stable chemically, and therefore are not altered during propellant processing and subsequent storage. This stability results in improved propellant ballistic repeatability and reliability. These new modifiers are adapted for applications in double base propellants made by the solvent or solventless process, where many current modifiers are inherently ineffective or are chemically unstable and therefore unsatisfactory.

The currently used modifiers are lead and copper compounds of salicylic and beta-resorcylic acids. They generally react with each other during propellant processing to produce a variety of products that are difficult to control, and they are often hydrolyzed by the processing solvents. Besides the obvious difficulty of obtaining reproducible propellant ballistic performance from batch-to-batch with current modifiers, some of the reaction products produced during processing and storage have a detrimental effect on the propellant performance. An example is the beta-resorcylic acid exudate problem of the DRAGON side thruster propellant.

The modifiers described in this invention disclosure can be substituted for the current modifiers in most double base propellants; thereby eliminating the instability problems. Moreover, certain of these new modifiers will produce propellant mesa and/or plateau burning rate characteristics with low $\pi_K$ in the pressure region of 5000 to 10,000 psi.

STRUCTURE AND PROPERTIES

A list of the most important ballistic modifiers is given in Table I below. Table I also shows the correct relative molar ratios of reactants to use for the preparation of each compound. The compounds all have the same general type of chelate structure, but they may be divided into two types. In the first type the modifier molecule contains two ligands of the same bidentate chelating agent, and in the second type the two bidentate ligands are different. The structures of both types of modifiers are illustrated in Table II below. Some of the modifiers also contain water of crystallization that can be removed at elevated temperature. Compound-1 for example, contains one water of crystallization at temperatures below 160° F., but is converted to the anhydrous form, shown in Table II at temperatures above 160° F.

TABLE I

REACTANTS AND THEIR RELATIVE PROPORTIONS FOR THE PREPARATION OF NEW BALLISTIC MODIFIERS

| Compound | Metal Ions, Grams - ions | | Chelating Agents, Gram - Moles | | | | | | |
|---|---|---|---|---|---|---|---|---|---|
| | $Cu^{++}$ | $Pb^{++}$ | 2,4-Dihydroxy-benzoic Acid | 2-Hydroxy-Benzoic Acid | 2,5-Dihydroxy-benzoic Acid | O-Acetamido-benzoic Acid | 4-Acetamido-Salicylic Acid | Salicylamide | Benzoic Acid |
| 1 | 1 | 1 | 2 | | | | | | |
| 2 | 1 | 1 | | 2 | | | | | |
| 3 | 1 | 1 | | | 2 | | | | |
| 4 | 1 | 1 | | | | 2 | | | |
| 5 | 1 | 1 | | | | | 2 | | |
| 6 | 1 | 1 | | | | | | 2 | |
| 7 | 1 | 1 | 1 | 1 | | | | | |
| 8 | 1 | 1 | 1 | | | 1 | | | |
| 9 | 1 | 1 | | 1 | | 1 | | | |
| 10 | 1 | 1 | 1 | | | | 1 | | |
| 11 | 1 | 1 | | 1 | | | 1 | | |
| 12 | 1 | 1 | 1 | | | | | 1 | |
| 13 | 1 | 1 | 1 | | | | | | 1 |
| 14 | 1 | 1 | | 1 | | | | | 1 |

TABLE II

CHEMICAL STRUCTURES OF SELECTED BALLISTIC MODIFIERS

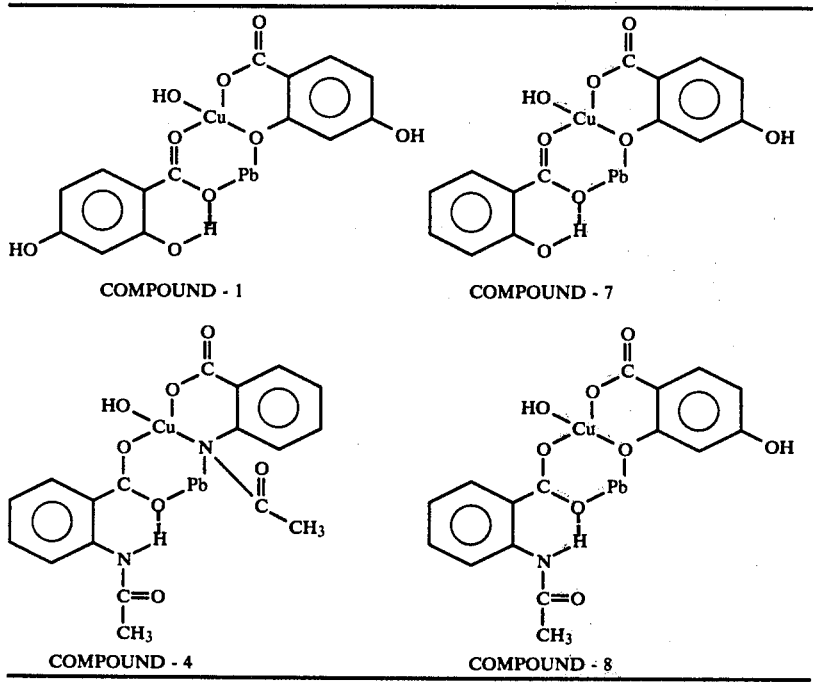

COMPOUND - 1     COMPOUND - 7

COMPOUND - 4     COMPOUND - 8

It is apparent from examining Tables I and II that a much larger number of ballistic modifier compounds can be synthesized by varying the types and combinations of the chelating agents, and possibly the metal ions and their valences. Based on past experience, the metal, lead, will probably be required in the compound for it to have ballistic activity. Although only compounds containing the metals, lead and copper, in their +2 valence states are illustrated, there are several other metals that may be used such as: silver, cobalt, nickel, zinc, and bismuth.

The properties of a particular ballistic modifier and hence its performance in propellants depends on the strengths and stabilities of the metal—ligand bonds. A major requirement for the synthesis of these ballistic modifiers is that one of the ligands must have two functional groups on an aromatic or heterocyclic ring, and one of the groups must be in an ortho position with respect to the other. The other ligand must have at least one functional group on an aromatic or heterocyclic ring. Furthermore, these functional groups must contain donor atoms capable of combining with the metal ions by donating a pair of electrons as shown in Table II. Each ligand may also contain one or more additional functional groups on the ring that do not enter into the synthesis reaction. These additional functional groups also affect the chemical and thermal stability of the modifier, and its reactivity with $NO_2$ radicals during propellant combustion. Consequently, ballistic modifiers can be tailored for specific propellant applications by modifying the structures of the ligands. Functional groups that may react with the metal ions by the replacement of hydrogen are: —COOH, —$SO_3H$, —OH (phenolic),

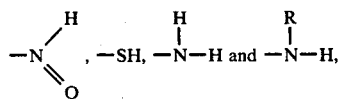

where R is an alkyl radical with from 1 to 20 carbon atoms.

Functional groups that may coordinate directly with the metal ions are: $=O$, $-NH_2$, $-NH$, $-N=$, $-O-R_1$, $=NOH$, $-OH$ (alcoholic), $-S-$ (thio ether), $-AsR_2$, and $-PR_2$ (R=alkyl radical with 1 to 20 carbon atoms, the two R's may be the same or different alkyl radicals).

All of the compounds in Table I are largely insoluble in water and most organic liquids. They are highly resistant toward hydrolysis and are thermally stable under nitrogen at temperatures in excess of 200° C. Compound 1, for example, is not affected chemically by boiling in water for 15 minutes and its solubility in boiling water is less than 0.1%. It is slightly soluble in dimethylformamide and pyridine, and is thermally stable under nitrogen at temperatures as high as 260° C.

SYNTHESIS

The relative proportions of the reactants for the synthesis of ballistic modifiers of this invention have been given in Table I. The general reaction equations are:

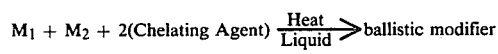

(1)

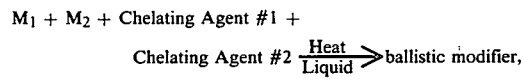

(2)

where $M_1$ and $M_2$ may be the same or different metal ions. Lead and copper in their +2 valence states are the preferred ions. The types of lead and copper compounds used have a significant influence on the quality of product obtained and its percentage yield. The preferred lead compound is lead (II) oxide (yellow form), and the preferred copper compounds are copper (II) hydroxide, and basic copper (II) carbonate. These compounds under the correct reaction conditions will yield ballistic modifiers having purities exceeding 98% by weight in yields of 90–100% by weight. Other compounds that can be used are the nitrates, acetates, sulfates, and chlorides of the metals. The use of these compounds, however, often results in side reactions, and impure products with substantially reduced yields. Water is the preferred reaction liquid. Organic liquids such as acetone and ethyl alcohol have been used, but they offer no apparent advantages over water.

Reactions are carried out in a vessel at atmospheric pressure by thoroughly agitating a mixture of the reactants in distilled or deionized water at elevated temperature until reaction is complete. The order of addition of the reactants must be controlled when the modifier being synthesized contains two different ligands. The optimum order of addition is predetermined for the specific modifier. Reaction temperatures from room temperature (25° C.) to 100° C. have been used, but the preferred temperature is 65° C. Although most of the modifiers can be synthesized at room temperature, the reaction time is unnecessarily long, and it is difficult to remove any unreacted starting materials because of their low solubility in the supernatant liquid. The reaction rate is accelerated at temperatures above 65° C. but the possibility of decomposing some of the chelating agents increases. This is particularly true for beta-resorcylic acid which can decompose to resorcinol. The normal reaction time at 65° C. for stoichiometric amounts of the reactants is three hours. This reaction time can be reduced to 0.5–1 hour by using a 5% by weight excess of the chelating agents. The use of nitric acid to reduce the pH of the reaction medium or sodium hydroxide to increase the pH is not recommended as these adjustments markedly lower the yields and often result in undesirable side reactions. The rate and extent of the reaction is continuously monitored by means of a recording pH meter. The reaction is complete when the reaction medium attains a constant pH value. The reaction slurry is filtered while hot to remove the product from the supernatant liquid, and the product is thoroughly washed with three equal portions of distilled water at 65° C. Filtrations of laboratory quantities of the modifier are made with a Buchner funnel using Whatman #42 filter paper. The modifier is then dried at 110° C. to a constant weight, and lightly ground in a mortar and pestle to a uniformly fine powder. In some cases the modifier may be dried to constant weight at a lower temperature to obtain the hydrated form of the modifier. As mentioned, copper (II) hydroxide and basic copper (II) carbonate are the preferred copper compounds. The carbonate is cheaper and generally of higher purity, but it produces carbon dioxide gas which results in foaming of the reaction mixture. The hydroxide is, therefore, recommended for the synthesis of large batches of the modifier when the forming produced by the carbonate cannot be tolerated.

Some of the modifiers listed in Table I can be synthesized from currently available modifiers, which are copper and lead compounds of substituted aromatic acids. This method of synthesis, however, is much less desirable than synthesis from the basic lead and copper salts and chelating agents previously described for the following reasons: (1) the number of different modifier types that can be prepared is very limited, (2) the stoichiometric quantities of the metals and chelating agents can generally not be obtained, and this results in undesirable side products; modifier products that are difficult to purify; and low yields, (3) current modifiers such as monobasic cupric salicylate and lead beta-resorcylate are more difficult to prepare reproducibly and in high purity than the modifiers in Table I, and (4) the cost of preparing the modifiers of this invention utilizing current modifiers instead of the basic raw materials, as shown in Table I, is considerably higher.

Examples of reactions with current modifiers to synthesize the ballistic modifiers of this invention are given in Table III below. Undesirable side products were obtained in each reaction. When the side products are water soluble, as is the case for reaction-1, it is possible to obtain a relatively pure compound, but the yield is low (60–70% by weight). Sometimes a mixture of modifiers of this invention is obtained as shown by reaction-6. Reaction-6 also illustrates the case where the current modifiers, monobasic cupric salicylate and monobasic lead beta-resorcylate, do not react in the laboratory under the conditions described unless an acid such as beta-resorcylic acid is added. These monobasic compounds have been found, however, by propellant analysis to react during propellant processing.

TABLE III
EXAMPLES OF NEW MODIFIER SYNTHESIS USING CURRENT MODIFIERS

1. Monobasic cupric salicylate + lead beta-resorcylate $\xrightarrow{\text{Heat}}{\text{H}_2\text{O}}$ Compound - 1 + other products.

2. Monobasic cupric beta-resorcylate + monobasic lead salicylate $\xrightarrow{\text{Heat}}{\text{H}_2\text{O}}$ Compound - 7 + other products + unreacted starting materials.

3. Normal cupric salicylate + monobasic lead beta-resorcylate $\xrightarrow{\text{Heat}}{\text{H}_2\text{O}}$ Compound - 2 + other products.

4. Monobasic cupric beta-resorcylate + normal lead salicylate $\xrightarrow{\text{Heat}}{\text{H}_2\text{O}}$ Compound - 7 + other products.

5. Monobasic cupric salicylate + normal lead salicylate $\xrightarrow{\text{Heat}}{\text{H}_2\text{O}}$ Compound - 2 + other products.

6. Monobasic cupric salicylate + monobasic lead beta-resorcylate + beta resorcylic acid $\xrightarrow{\text{Heat}}{\text{H}_2\text{O}}$ Compound - 1 + Compound - 7 + other products.

NOTE:
Refer to Tables I and II for identification of the compounds formed.

The following reactions illustrate the synthesis of selected ballistic modifiers of this invention using basic starting materials:

EXAMPLE 1

Using a total of 10 g of reactants, Compound-1 was synthesized according to the following reaction:

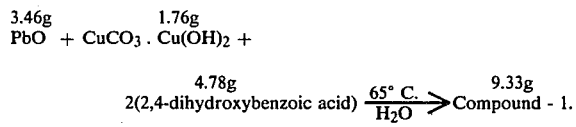

$$\begin{array}{cc} 3.46g & 1.76g \\ \text{PbO} & + \text{CuCO}_3 \cdot \text{Cu(OH)}_2 + \end{array}$$

$$\underset{2(2,4\text{-dihydroxybenzoic acid})}{4.78g} \xrightarrow[\text{H}_2\text{O}]{65°\text{ C.}} \underset{\text{Compound - 1.}}{9.33g}$$

The lead (II) Oxide (yellow form) was reagent grade, and the 2,4-dihydroxybenzoic acid (beta-resorcylic acid) was practical grade. These chemicals were assumed to be pure. The basic copper (II) carbonate and a copper assay of 55.8% by weight, and this assay value was used to determine the weight of basic copper (II) carbonate for the reaction. The reactants were weighed into a 250 ml graduated beaker, and 50 ml of distilled water was added. The mixture was stirred at room temperature (25° C.) to thoroughly wet the reactants, then additional distilled water was added to bring the total volume to the 200 ml mark. The reaction slurry was vigorously stirred throughout the remainder of the reaction by means of a Teflon coated magnetic stirring bar and the pH of the slurry was continuously recorded. An equilibrium pH of 3.8 was established at room temperature, then the slurry was heated to the reaction temperature of 65° C. The initial application of heat resulted in partial solution of the 2,4-dihydroxybenzoic acid which lowered the pH to 3.6. Immediately after this initial lowering of the pH, the reaction rate began to increase thereby gradually increasing the pH during the remainder of the reaction. The reaction was completed 3.5 hours after addition of the reactants, as indicated by the attainment of a constant pH of 5.45. The hot slurry was then filtered using a Buchner funnel and a Whatman #42 filter paper. The residue (Compound-1) was washed with three 100 ml portions of distilled water at 65° C. and dried to constant weight in an oven at 160° F. The dried modifier was lightly ground with a mortar and pestle to break up agglomerates and produce a fine light green powder. The yield was 98.6%, and subsequent chemical analysis of the modifier showed that its purity was greater than 98% by weight.

EXAMPLE 2

The procedure of example 1 was repeated in this example except that the reaction was carried out at room temperature (25° C.). The time required for complete reaction to take place was 8 hours, and the pH increased from an initial value of 3.75 to a final value of 6.55. The modifier residue was washed with distilled water at 25° C. as described in example 1. The dried modifier weight was 9.32 g which corresponds to a yield of 98.5%. The purity of the modifier was slightly less than that of example 1. A portion of the modifier dried at 160° F. was further dried at 110° C., where it lost approximately 3% by weight, corresponding to one water of hydration.

EXAMPLE 3

The procedure of example 1 was repeated in this example except that a 5% excess of 2,4-dihydroxybenzoic acid by weight was used. The reaction was:

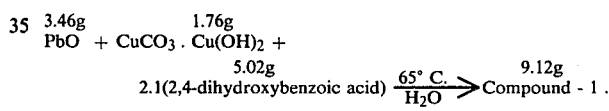

$$\begin{array}{cc} 3.46g & 1.76g \\ \text{PbO} & + \text{CuCO}_3 \cdot \text{Cu(OH)}_2 + \end{array}$$

$$\underset{2.1(2,4\text{-dihydroxybenzoic acid})}{5.02g} \xrightarrow[\text{H}_2\text{O}]{65°\text{ C.}} \underset{\text{Compound - 1.}}{9.12g}$$

The time required for complete reaction to take place was 1.75 hours. The initial value of the pH was 3.30 and the final value was 3.95. The excess acid was soluble in the filtrate, and was completely removed from the residue (Compound-1) by washing with distilled water at 65° C. The yield of Compound-1, dried at 160° F., was 96.4%, and its purity was greater than 98% by weight.

EXAMPLE 4

In this experiment, Compound-1 was made on a 50 g scale according to the following reaction:

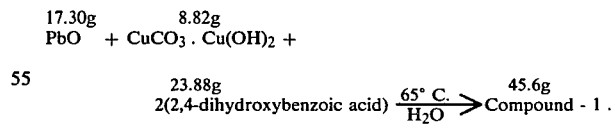

$$\begin{array}{cc} 17.30g & 8.82g \\ \text{PbO} & + \text{CuCO}_3 \cdot \text{Cu(OH)}_2 + \end{array}$$

$$\underset{2(2,4\text{-dihydroxybenzoic acid})}{23.88g} \xrightarrow[\text{H}_2\text{O}]{65°\text{ C.}} \underset{\text{Compound - 1.}}{45.6g}$$

The steps of the procedure were the same as for Example 1 except that the reaction was carried out in an 800 ml beaker, and 600 ml of distilled water was used. The initial pH of the reaction mixture at room temperature was 3.60, and at the completion of the reaction was 5.60. The time required for complete reaction was 2.5 hours after addition of the reactants. The product was dried to constant weight at 160° F. and ground to a fine light green powder. The yield was 96.3% and the purity of the compound was greater than 99% by weight.

EXAMPLE 5

This example describes the synthesis of Compound-2 on a 10 g scale according to the following reaction:

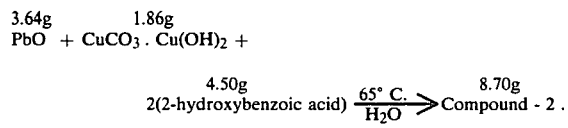

The steps of the procedure were the same as those of Example 1. The initial pH of the reaction mixture at 24° C. was 5.25. The reaction began to take place immediately, and leveled off at a pH value of 4.75 at 24° C. Heat was then applied to the reaction mixture; whereupon an additional portion of the 2-hydroxybenzoic acid dissolved thereby lowering the pH of the slurry to 3.88 at the reaction temperature of 65° C. After 40 minutes of mixing, the pH of the slurry began to slowly increase as the reaction progressed. The pH attained a constant value of 4.68 after three hours reaction time indicating that the reaction was complete. The product was removed by filtration and dried to a constant weight at 110° C. The dried powder was ground in a mortar and pestle to break up agglomerates, and weighed to determine the yield. The yield was 95.0%. Analysis of the compound indicated that its purity was greater than 95% by weight.

EXAMPLE 6

This experiment was a repeat of Example 5 except that a 5% by weight excess of the 2-hydroxybenzoic acid was used. This has the advantage of increasing the rate of reaction, and providing greater assurance that the copper and lead salts will completely react. Care must be exercised, however, to wash the excess acid from the desired product. The reaction was:

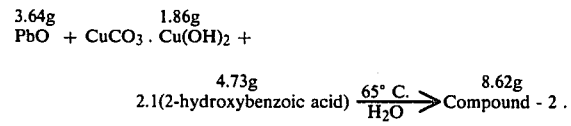

The steps in the procedure were the same as those given in Example 1. The initial pH of the reaction slurry at 25° C. was 3.90. Heat was applied to raise the temperature of the reaction to 65° C. The reaction was complete after 30 minutes. The final pH of the slurry was 3.31. The product was removed from the supernatant liquid by filtration, dried to a constant weight at 110° C., and ground to a fine powder. The yield was 94.1%. The purity of the compound was greater than 99% by weight.

EXAMPLE 7

This example describes the synthesis of Compound-7, and is typical of the procedure required to synthesize those modifiers containing two different ligands in the molecule. The reaction was:

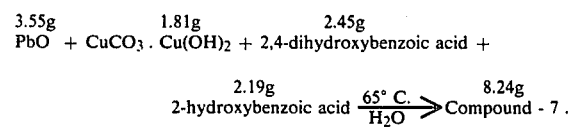

Since two different chelating agents are used, the order in which the reactants are added to the reaction vessel must be controlled to avoid undesirable side reactions. The order of addition given here is one of several that can be used to prepare pure Compound-7. The basic copper (II) carbonate; 2,4-dihydroxybenzoic acid; and 2-hydroxybenzoic acid were added along with 50 ml of distilled water to a 250 ml beaker, and the mixture was stirred to thoroughly wet the solids. The total volume of the slurry was then adjusted to 200 ml with distilled water, and heated to 65° C. The reaction mixture was vigorously stirred and the pH was continuously recorded during the reaction. The pH equilibrated at 3.28, and 20 minutes after addition of the first three reactants the lead (II) oxide was added. The pH then gradually increased as the reaction progressed and attained a constant value of 4.70. The total reaction time was 2 hours. The slurry was filtered using a Buchner funnel and Whatman #42 filter paper. The residue (Compound-7) was then dried to a constant weight at 110° C., and ground in a mortar and pestle to break up agglomerates. The yield of Compound-7 was 90.0%, and its purity was greater than 99% by weight.

EXAMPLE 8

This example illustrates the synthesis of Compound-8, which contains two different ligands. In the case of this particular compound, all of the reactants can be added to the reaction vessel at the same time. The following reaction was carried out:

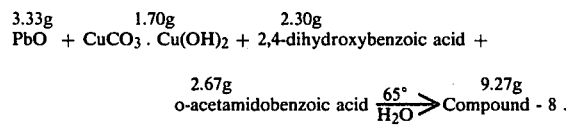

The steps of the procedure were the same as given in Example 1. The initial pH of the reaction mixture at 24° C. was 4.30. The reaction immediately began to take place at 24° C. and as a result the pH increased. When the reaction had proceeded for 20 minutes and the pH had increased to 5.9, heat was applied to the reaction mixture. The pH then decreased to 4.65, after which it increased again to a final constant value of 6.10. The total reaction time from addition of the reactants was 1.5 hours. The slurry was filtered and the residue (Compound-8) was dried to a constant weight at 110° C., and ground in a mortar and pestle. The yield of Compound-8 was 94.7%.

EXAMPLE 9

This example describes the synthesis of Compound-1 by using current ballistic modifiers according to the reaction:

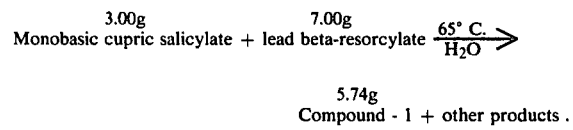

The foregoing 1:1 molar stiochiometry of the reactants is the closest that can be obtained to the true stoichiometry for compound-1. Nevertheless, the reaction produces a mole of salicylic acid which is not required, and which may enter into undesirable side reactions. The steps of this synthesis were the same as those of Example 1. The initial pH of the reaction mixture at room temperature (25° C.) was 4.50. After 20 minutes of mixing, the pH dropped to 4.00 at which time heat was applied. The pH leveled off at 3.25 after 40 minutes at which time the temperature of the reaction medium had equilibrated at 70° C., and the reaction was complete. The yield of Compound-1 was 68.6% and its purity was greater than 98% by weight.

PROPELLANT APPLICATIONS

Compounds-1 and -7 have been evaluated in double base type propellants. The nominal compositions of the propellants are given in Table IV below. All the propellant compositions were made by a standard solventless process. The burning rates of each composition as a function of pressure were determined with cured propellant strands, and the heat of explosion was also determined. The compositions containing Compound-1 had ballistic performance comparable to that of a double base propellant containing monobasic cupric salicylate and lead beta-resorcylate modifiers. Composition-A containing 4% of Compound-1 had burning rates on the low side of the specification. Composition-B had higher and more acceptable burning rates than Composition-A. Neither composition has been observed to form exudate on the propellant surface during storage, as is the case with many compositions containing monobasic cupric salicylate and lead beta-resorcylate. These experiments demonstrated that Compound-1 can be substituted for the current ballistic modifiers of one or more double base propellants, resulting in improved ballistic repeatability and storage stability. As anticipated, Composition-C which contained Compound-7 had mesa burning rate characteristics at a lower pressure than the compositions containing Compound-1. Composition-D had burning rate characteristics intermediate to those of the other compositions. Composition-E had strand burning rates at the specified temperatures of the propellant as depicted in FIG. 1 of the drawing, and Composition-F had strand burning rates at the specified temperatures as depicted in FIG. 2 of the drawing.

The other compounds in Table I may be used as ballistic modifiers to act as catalysts in double base propellants. For example, compounds containing salicylates produce mesa and/or plateau burning characteristics at low pressures; whereas those containing resorcylates produce comparable characteristics at higher pressures. Some of the compounds in Table I such as Compounds-8 and -10, have the potential of reducing temperature sensitivity and producing mesa and/or plateau burning rate characteristics at pressures in the region between 4000 psi and 10,000 psi.

lected from the group consisting of lead, copper, silver, cobalt, nickel, zinc and bismuth with from one to two chelating agents in the presence of a reaction liquid selected from the group consisting of water, acetone and alcohol to produce a reaction slurry; stirring said reaction slurry until a constant pH is obtained; and filtering said reaction slurry to separate the reaction product.

2. The process of claim 1, wherein said chelating agents are selected from the group consisting of 2,4-dihydroxybenzoic acid, 2-hydroxybenzoic acid, 2,5-dihydroxybenzoic acid, o-acetamidobenzoic acid, 4-acetamido salicylic acid, salicylamide and benzoic acid.

3. The process of claim 2 wherein said reaction is carried out with a 1:1 molar ratio of the selected metal ions to the chelating agent.

4. The process of claim 2 wherein said reaction is carried out with a 5% excess of chelating agent to metal ions on a molar ratio.

5. The process of claim 3, wherein said selected metal ions consist of lead and copper and said selected chelating agent consists of 2,4-dihydroxybenzoic acid.

6. The process of claim 3, wherein said selected metal ions consist of lead and copper and said selected chelating agent consists of 2-hydroxybenzoic acid.

7. The process of claim 3, wherein said selected metal ions consist of lead and copper and said selected chelating agent consists of 2,4-dihydroxybenzoic acid and 2-hydroxybenzoic acid.

8. The process of claim 3, wherein said selected metal ions consist of lead and copper and said selected chelating agent consists of 2,4-dihydroxybenzoic acid and o-acetamidobenzoic acid.

9. The process of claim 3, wherein said selected metal ions consist of lead and copper and said selected chelating agent consists of 2,4-dihydroxybenzoic acid and 4-acetamidosalicylic acid.

10. The process of synthesizing ballistic modifiers, said process consisting of mixing a salicylate compound and a resorcylate compound on a 1:1 molar ratio in a reaction liquid selected from the group consisting of water, acetone, and alcohol, wherein one of said compounds contains copper and the other of said compounds contains lead to form a reaction slurry, stirring said reaction slurry until a constant pH is obtained, and filtering said reaction slurry to separate the ballistic modifiers from undesirable impurities.

11. The process of claim 10, wherein said salicylate compound is monobasic cupric salicylate and said resorcylate compound is lead beta-resorcylate.

12. A ballistic modifier composition, for use in solid propellants, said ballistic modifier composition consist-

TABLE IV

NOMINAL COMPOSITIONS OF HEN-12 TYPE DOUBLE BASE PROPELLANTS CONTAINING COMPOUNDS - 1 AND - 7

| Ingredients | Composition - A | Composition - B | Composition - C | Composition - D | Composition - E | Composition - F |
|---|---|---|---|---|---|---|
| Nitrocellulose (12.6 N) | 49.0 ± 1.5 | 49.0 ± 1.5 | 49.0 ± 1.5 | 49.0 ± 1.5 | 49.0 ± 1.5 | 49.0 ± 1.5 |
| Nitroglycerine | 40.6 | 40.6 | 40.6 | 40.6 | 40.6 | 40.6 |
| Di-n-propyl adipate | 3.3 | 3.3 | 3.3 | 3.3 | 3.3 | 3.3 |
| 2-nitrodiphenylamine | 2.0 ± 0.5 | 2.0 ± 0.5 | 2.0 ± 0.5 | 2.0 ± 0.5 | 2.0 ± 0.5 | 2.0 ± 0.5 |
| Candelilla wax | 0.1 | 0.1 | 0.1 | 0.1 | 0.1 | 0.1 |
| *Compound - 1 | 4.0 | 4.5 | | 4.0 | 5.0 | |
| *Compound - 7 | | | 4.0 | 1.0 | | 5.0 |

*The compositions of these compounds are identified in Table I.

We claim:

1. The process of synthesizing ballistic modifiers, said process consisting of mixing different metal ions seing of the reaction product formed by mixing different metal ions selected from the group consisting of lead, copper, silver, cobalt, nickel, zinc and bismuth with from one to two chelating agents in the presence of a reaction liquid selected from the group consisting of water, acetone and alcohol to produce a reaction slurry; stirring said reaction slurry until a constant pH is obtained; and filtering said reaction slurry to separate the reaction product.

13. A ballistic modifier composition as set forth in claim 12, wherein said selected metal ions consist of lead and copper and said selected chelating agent consists of 2,4-dihydroxybenzoic acid.

14. A ballistic modifier composition as set forth in claim 12, wherein said selected metal ions consist of lead and copper and said selected chelating agent consists of 2-hydroxybenzoic acid.

15. A ballistic modifier composition as set forth in claim 12, wherein said selected metal ions consist of lead and copper and said selected chelating agent consists of o-acetamidobenzoic acid.

16. A ballistic modifier composition as set forth in claim 12, wherein said selected metal ions consist of lead and copper and said selected chelating agent consists of 2,4-dihydroxybenzoic acid and 2-hydroxybenzoic acid.

17. A ballistic modifier composition as set forth in claim 12, wherein said selected metal ions consist of lead and copper and said selected chelating agent consists of 2,4-dihydroxybenzoic acid and o-acetamidobenzoic acid.

18. A ballistic modifier composition as set forth in claim 12, wherein said selected metal ions consist of lead and copper and said selected chelating agent consists of 2,4-dihydroxybenzoic acid and 4-acetamidosalicylic acid.

* * * * *